Jan. 19, 1971 E. S. BOERNER Plant Pat. 3,018
ROSE PLANT
Filed Dec. 20, 1968
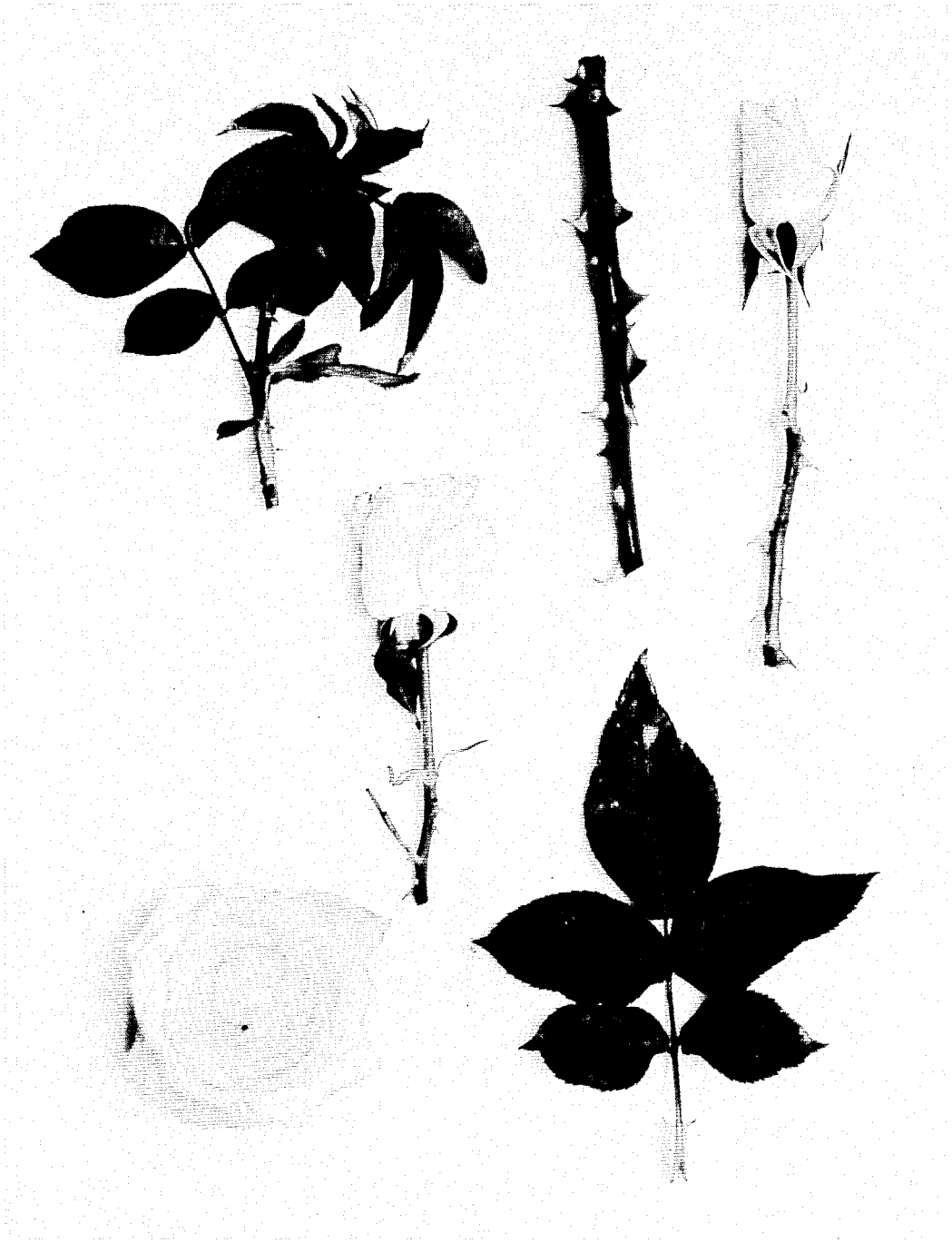
Inventor.
E. S. Boerner, Deceased
By: Lincoln Rochester Trust Company
By: Edward L. Jenner, Trust Officer
and Roger L. Boerner,
Executors
By: Robb & Robb, Attorneys United States Patent Office Plant Pat. 3,018
Patented Jan. 19, 1971

3,018
ROSE PLANT

Eugene S. Boerner, deceased, late of Benton, N.Y., by Lincoln Rochester Trust Company, Rochester, N.Y., and Roger L. Boerner, Milwaukee, Wis., executors, assignors to Jackson & Perkins Company, Newark, N.Y., a corporation of New York Filed Dec. 20, 1968, Ser. No. 785,816
Int. Cl. A01h 5/00
U.S. Cl. Plt.—11 1 Claim The present invention relates to a new and distinct variety of rose plant of the hybrid tea class, which was originated by the late Eugene S. Boerner, deceased, by crossing the rose variety known as "Revelry" (Plant Pat. No. 1,850) with the rose variety known as "Hawaii" (Plant Pat. No. 1,833), the former being the seed parent and the latter being the pollen parent.

The primary objective of this breeding was to produce a new rose variety having foliage and floriferousness habits similar to those of the variety "Hawaii," but which bears flowers of a different color. This objective was fully achieved, along with other improvements, as evidenced by the following unique combination of characteristics which are outstanding in the new variety and which distinguish it from its parents, as well as from all other rose varieties:

(1) An upright and floriferous plant habit;

(2) Distinctive and attractive foliage, with oval leaflets having a long pointed tip;

(3) Well formed and high-centered blooms; and (4) A distinctive and attractive pink flower color which is generally Dawn Pink when viewed from a distance.

Asexual reproduction of the new variety by budding, as performed at both Livermore and Wasco, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Wilson's Horticultural Colour Chart, except where general color terms of ordinary dictionary significance are obvious:

Parentage: Seedling.
*Seed parent.*—"Revelry."
*Pollen parent.*—"Hawaii."
Classification:
*Botanic.*—Rosa.
*Commercial.*—Hybrid tea.
Propagation: Holds its distinguishing characteristics through succeeding propagations by budding.

FLOWER (Observations made from specimens grown at Newark, N.Y., in the morning during the middle of the month of September.)
Blooming habit: Continuous.
Bud:
*Size.*—Medium.
*Form.*—Short, with flat top.
*Color.*—When sepals first divide: Spinel Red, Plate 0023/3. When half-blown: Inside of petals—Spinel Red, Plate 0023/2; reverse of petals—Spinel Red, Plate 0023/3, with lower portions lighter and blending to Naples Yellow, Plate 403/3 at base.

*Sepals.*—Inside: Covered with white tomentum. Outside: Serrated.
*Receptacle.*—Color: Light green. Shape: Apple. Size: Broad. Surface: Smooth.
*Peduncle.*—Length: Medium. Surface: Prickly. Color: Light green.
*Opening.*—Petals roll back spiral fashion, with outer petals first leaving a high center.
Bloom:
*Size.*—Medium.
*Borne.*—Singly.
*Stems.*—Medium length.
*Form.*—High-centered; outer petals curl back.
*Petalage.*—Number of petals under normal conditions: From about 25 to 30.
*Color.*—Center of flower: Rhodonite Red, Plate 0022/1. Inside of petals: Rose Madder, Plate 23/3, lightened with Dawn Pink, Plate 523/3. Reverse of petals: Dawn Pink, Plate 523/2. Base of petals: Naples Yellow, Plate 403/3. General tonality from a distance: Dawn Pink, Plate 523. Variegations: None. Discoloration: General tonality at end of first day—Dawn Pink, Plate 523. Third day—Dawn Pink, Plate 523/2.
*Fragrance*: Slight.
Petals:
*Texture.*—Leathery.
*Surface.*—Satiny.
*Form.*—Round.
*Arrangement.*—Imbricated.
*Petaloids in center.*—Few.
*Persistence.*—Drop off cleanly.
*Lasting quality.*—On the plant: Long. As cut flower: Fair.

REPRODUCTIVE ORGANS

Anthers: Medium number.
*Color.*—Yellow.
*Arrangement.*—Regularly arranged around styles.
Filaments (threads): Some medium length and some short.
Pollen:
*Color.*—Lemon yellow.
Styles: Loosely separated; uneven length.
Stigmas:
*Color.*—White.
Ovaries: All enclosed in calyx.
Hips: None observed.
Seeds: None observed.

PLANT

Form: Bush.
Growth: Vigorous.
Foliage: Compound of 5 leaflets.
*Size.*—Large.
*Quantity.*—Normal.
*Color.*—New foliage: Bronzy on both sides. Old foliage: Dark green on upper side and slightly lighter on under side.
*Shape.*—Oval pointed.
*Texture.*—Upper side: Leathery. Under side: Smooth.
*Ribs and veins.*—Ordinary.
*Edge.*—Serrated.
*Serrations.*—Single.
*Petiole.*—Color: Reddish. Under side Prickly.
*Stipules.*—Short. Color: Yellowish green.
*Disease resistance.*—Resistant to ordinary rose diseases, as determined by comparison with other rose varieties grown under the same conditions at Newark, N.Y.
Wood:
*New wood.*—Color: Light green. Bark: Smooth.

*Old wood.*—Color: Green. Bark: Smooth.

Thorns:

*Quantity.*—On main stalks from base: Ordinary. On laterals from stalk: Ordinary.

*Form.*—Long base; medium length; hooked downward.

*Color (when young).*—Pale brown.

*Position.*—Irregular.

Prickles:

*Quantity.*—On main stalks: Few. On laterals: Few.

*Color.*—Brown.

What is claimed is:

1. A new and distinct variety of rose plant of the hybrid tea class, substantially as herein shown and described, characterized particularly as to novelty by the unique combination of an upright and floriferous plant habit, distinctive and attractive foliage, with oval leaflets having a long pointed tip, well formed and high-centered glooms, and a distinctive and attractive pink flower color which is generally Dawn Pink when viewed from a distance.

No references cited.

ROBERT E. BAGWILL, Primary Examiner